United States Patent [19]

Sabourin et al.

[11] 4,204,078

[45] May 20, 1980

[54] PROCESS FOR THE PREPARATION OF NITROPHENYL HYDROXY SUBSTITUTED ACETYLENS

[75] Inventors: Edward T. Sabourin, Allison Park; Charles M. Selwitz, Monroeville, both of Pa.

[73] Assignee: Gulf Reserach and Development Company, Pittsburgh, Pa.

[21] Appl. No.: 942,068

[22] Filed: Sep. 13, 1978

[51] Int. Cl.$^2$ .............................................. C07C 33/04
[52] U.S. Cl. ..................................... 568/705; 568/939
[58] Field of Search ........................ 260/645; 568/705

[56] References Cited

U.S. PATENT DOCUMENTS 4,016,214   4/1977   Douglas et al. ................. 260/645 X

*Primary Examiner*—Leland A. Sebastian

[57] ABSTRACT

Nitrophenylacetylene and certain precursors to nitrophenylacetylene are prepared in improved yields by reacting a nitrobromobenzene with a substituted terminal acetylene compound containing at least three carbon atoms and a hydroxy group on the carbon atom adjacent to the acetylene group in the presence of a dialkyl or trialkyl amine solvent and a catalyst system consisting of a palladium complex containing two halogen moieties and two tri-substituted phosphine moieties and some excess trisubstituted phosphine compounds.

21 Claims, No Drawings

PROCESS FOR THE PREPARATION OF NITROPHENYL HYDROXY SUBSTITUTED ACETYLENS

This invention relates to an improved process for producing nitrophenyl hydroxy substituted acetylenes in improved yields and in particular for producing 2-methyl-4(3-nitrophenyl)3-butyn-2-ol.

BACKGROUND OF THE INVENTION

The recent introduction of acetylene-terminated polyimides to produce cured reaction products which are stable at very high temperatures of 450° C. and up has created an interest and need to produce the polyimides at attractive and competitive costs. The prime difficulty in the preparation of the acetylene-terminated polyimides which are described, for example, in U.S. Pat. No. 3,845,018 and U.S. Pat. No. 3,879,349, both to Norman Bilow et al, is the preparation of the monomers which include in one instance the preparation of meta-aminophenylacetylene (APA).

In Ser. No. 840,553 filed in the U.S. Patent Office in the names of E. T. Sabourin and C. M. Selwitz on Oct. 11, 1977, now U.S. Pat. No. 4,128,588, an improved procedure is described for the preparation of precursors to nitrophenylacetylenes (NPA), which NPA is a precursor to APA. In accordance with the teachings of Ser. No. 840,553, nitrophenyl hydroxy substituted acetylenes are prepared from nitrobromobenzene by the reaction of the nitrobromobenzene with a substituted terminal acetylene compound containing at least 3 carbon atoms and a hydroxy group on the carbon atom adjacent to the acetylene group at mild conditions to produce a substantial yield of a nitrophenyl hydroxy substituted acetylene. The reaction occurs in the presence of an amine-type solvent, which serves not only as a solvent but as a complexing agent with the by-product HBr, which is produced during the reaction. The substitution reaction is catalyzed by a complex palladium salt containing two halogen moieties and two substituted phosphine moieties where the substituents on the phosphorus are phenyl, lower alkyl groups and substituted phenyl groups. The catalytic activity of the palladium complex salt is promoted with a small amount of cuprous iodide.

While the process described in Ser. No. 840,553 represents a substantial advance over the prior art techniques which are described in the opening pages of Ser. No. 840,553, the process, on scale-up, was found to be sluggish after initial high reaction rates which eventually resulted in insufficient conversion in normal and desirable commercial reaction times, i.e. less than four hours. In addition, unwanted higher boiling by-products in undesirable amounts were formed, resulting in lowered selectivities of the process to the desired nitrophenyl substituted acetylenes. The unwanted by-products and unreacted charge materials are difficult to remove from the reaction product to produce products of sufficient purity for their direct use in the production of the acetylene terminated polyimides described in the Bilow et al patents referred to above. Product recovery is difficult because the reaction product which contains an $NO_2$ group is thermally unstable, which prohibits the use of distillation for separation even at reduced pressures or with steam. Fractional crystallization also proved to be unfeasible on products which contained about 15 percent of unreacted charge materials and higher boiling by-products.

It has now been found in accordance with the invention that improved yields of nitrophenyl hydroxy substituted acetylenes can be prepared from nitrobromobenzene by reaction of the nitrobromobenzene with a substituted terminal acetylene compound containing at least three carbon atoms and a hydroxy group on the carbon atom adjacent to the acetylene group at mild conditions. The reaction occurs in the presence of an amine type solvent; a catalyst comprising a complex palladium salt containing two halogen moieties and two substituted phosphine moieties; a promoter comprising a small amount of cuprous iodide; and a sufficient amount of an excess triphenyl phosphine over that amount needed to form the palladium catalyst to result in a yield of desired nitrophenyl hydroxy substituted acetylene of at least 90 weight percent and usually in excess of 95 weight percent. In one preferred embodiment of this invention, the desired nitrophenyl hydroxy substituted acetylene can be recovered in substantially pure form by fractional crystallization of the reaction product.

Any nitrobromobenzene can suitably be employed in the process of this invention. The source of the nitrobromobenzene or its method of preparation are well known in the art and are not critical to the operation of the process of this invention. The suitable nitrobromobenzenes are, of course, the ortho-, meta- and para-nitrobromobenzenes; and of these, meta-nitrobromobenzene is preferred.

The nitrobromobenzene is reacted with a substituted terminal acetylene compound containing at least 3 carbon atoms and a hydroxy group on the carbon atom adjacent to the acetylene group. The preferred substituted terminal acetylene compounds are those having the formula:

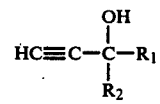

where $R_1$ and $R_2$ can be the same or different and are selected from the group consisting of hydrogen, lower alkyl groups having from 1 to 4 carbon atoms, phenyl, substituted phenyl; or where $R_1$ and $R_2$ can form a saturated 5- or 6-membered ring. The preparation of these compounds is well known in the art and forms no part of the subject invention. For example, acetylene can be reacted with acetone to form 2-methyl-3-butyn-2-ol, which is the preferred substituted terminated acetylenic charge stock for use in the process of this invention. Other suitable acetylenic compounds include the following:
3-methyl-1-pentyn-3-ol;
3-ethyl-1-pentyn-3-ol;
2-phenyl-3-butyn-2-ol;
1-ethynylcyclohexanol; and
1-ethynolcyclopentanol.

Usually the nitrobromobenzene is reacted with the terminal acetylene compounds in a molar ratio of about 1:1, but suitable molar ratios include those from 1:0.5 to 1:100 and are more preferably from 1:1 to 1:5.

The reaction of the nitrobromobenzene with the terminal acetylenic compounds defined above occurs in the presence of a dialkyl or trialkyl amine solvent and a complex catalyst system. The amine solvent can suitably have the formula:

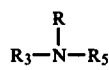

where $R_3$, $R_4$ and $R_5$ can be the same or different and are selected from the group consisting of hydrogen and lower alkyl groups having from 1 to 4 carbon atoms, with the proviso that no more than one of said R groups can be hydrogen. Suitable solvents include but are not limited to dimethylamine, trimethylamine, diethylamine, triethylamine, ethylpropylamine, ethylbutylamine and dibutylamine.

The catalyst employed is a complex palladium salt containing two halogen moieties, where the halogen is selected from the group consisting of bromine, iodine and chlorine, and two trisubstituted phosphine moieties where the constituents are selected from phenyl, alkyl groups having from 1 to 4 carbon atoms, and substituted phenyl groups. A suitable palladium complex would have the formula:

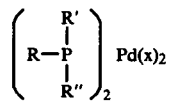

where x is bromine, iodine or chlorine, and R, R' and R" are the same or different and are selected from the group consisting of phenyl, alkyl groups having from 1 to 4 carbon atoms and substituted phenyl groups. The substituents on the phenyl groups can include alkyl groups having from 1 to 4 carbon atoms, alkoxy groups having 1 to 4 carbon atoms, and halogen. A suitable list of representative palladium complex salts which can be employed in the process of this invention include:
bis(triphenylphosphine)palladium dibromide;
bis(tri-n-butylphosphine)palladium dichloride;
bis(tri-t-butyl-phosphine)palladium dichloride;
bis(tri-i-butylphosphine)palladium dichloride;
bis(triethylphosphine)palladium dichloride;
bis(tripropylphosphine)palladium dichloride;
bis(tritolylphosphine)palladium dichloride;
bis(trianisylphosphine)palladium dichloride;
bis(tri(chlorophenyl)phosphine)palladium dichloride; and
bis(tri(bromophenyl)phosphine)palladium dichloride.

The palladium catalyst can be added to the reaction mixture as such or can be formed in situ in the reaction mixture by the separate addition of a palladium salt having the formula $Pd(X)_2$ where X is as defined, and a trisubstituted phosphine compound having the formula:

where R, R' and R" are as defined and wherein the molar ratio of the trisubstituted phosphine to the palladium is about 2:1. It has been found in accordance with the invention that the presence of excess trisubstituted phosphine, e.g. triphenylphosphine, over and above that necessary to form the palladium catalyst results in an overall yield of the desired nitrophenyl substituted acetylenes of over 90 weight percent, usually over 95 weight percent. Another manner of stating the above is that the addition of the excess trisubstituted phosphine results in reduced total reaction times for substantially complete reaction of the nitrobromobenzene and/or an improved selectivity to the formation of the desired nitrophenyl substituted acetylenes.

Whether the palladium catalyst is formed in situ or whether the palladium catalyst is formed separately and added to the reaction system, the molar ratio of the trisubstituted phosphine compound to palladium in the reaction system must be above 2:1, and is usually from 2.5:1 to 50:1, more preferably from 2.5:1 to 25:1, and most preferably from 5:1 to 20:1. It has been found that as the molar ratio of trisubstituted phosphine to palladium increases over about 20:1, both the overall reaction time tends to increase and the selectivity tends to decrease.

A promoter for the catalyst system is also employed, and this promoter comprises cuprous iodide. Usually the amount of the promoter is very small, and suitable amounts of promoter include a molar ratio of promoter to palladium catalyst of from 0.5:1 to 20:1, preferably from 1:1 to 5:1. The amount of the palladium catalyst employed in the reaction is usually from 0.01 to 1.0 mole percent based on nitrobromobenzene and is more preferably from 0.02 to 0.05 mole percent based on nitrobromobenzene.

The reaction of the nitrobromobenzene with the acetylene-terminated compound is really a substitution-type reaction, and the reaction conditions to employ are relatively mild and include a temperature from about 20° to 200° C. and more preferably from 50° to 125° C. However, it is considered that the reaction conditions are not critical, and the precise reaction conditions to employ would be obvious to one having ordinary skill in the art. The reaction conditions should be such that the solvent chosen is maintained in the liquid phase. The normal reaction pressure is atmospheric; however, increased reaction pressures of up to 250 psig (1.7 MPa) or higher can be employed. The reaction time to employ is somewhat dependent on the particular charge stock and catalyst chosen and, of course, on the reaction temperature. Usually the reaction time is from 1 hour to 20 hours, but is more usually from 1 hour to 12 hours. Higher or lower reaction times can be employed, for timing is not a critical parameter but rather in many cases serves to increase the yield of the desired reaction product.

A typical reaction sequence is shown in Equation 1 below, which utilizes certain specific charge stocks which fall within the scope of the charge stocks defined above.

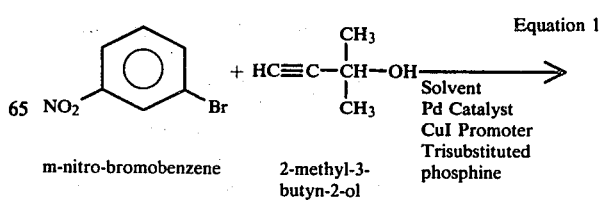

Equation 1

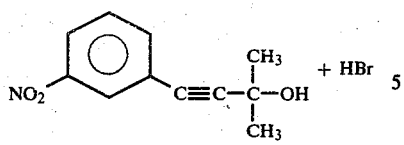

+ HBr

Referring to Equation 1 above, it can be seen that a by-product of the reaction sequence is HBr. The HBr cannot be permitted to remain in the reaction product because of its corrosive nature.

It is one of the purposes of the amine solvent to react with the HBr in order to produce the amine hydrobromide salt and render it inactive. The amount of the amine solvent to employ in the reaction is not critical but must thus be sufficient to maintain the reactants in the liquid phase plus provide sufficient amine to react with the by-product HBr. Amounts of solvent from 500 to 700 ml per mole of nitrobromobenzene have successfully been employed. However, greater or lesser amounts can be employed, and the particular amount to employ would be within the normal skill in the art given the criteria set forth above.

The invention will be further described with reference to the following experimental work.

EXAMPLE 1

In a 5.1 round bottom flask, equipped with a mechanical stirrer, condenser, thermometer, a rubber septum to allow sampling, and a nitrogen purge system, was placed 606 grams of m-bromonitrobenzene, 340 grams 2-methyl-3-butyn-2-ol, 2000 ml triethylamine, and 0.5 grams of bis-triphenyl phosphine palladium dichloride.

The system was purged with nitrogen, and 0.5 grams of cuprous iodide was added, and the temperature raised to ca. 90° to 95° C. At intervals, small aliquots were removed and analyzed by gas chromatography. After three hours, approximately two-thirds of the bromonitrobenzene (BNB) had been consumed. The reaction was allowed to continue for a total of 11 hours. The conversion of bromonitrobenzene was 84.7% at this point. The mixture contained 464.4 grams of 2-methyl-4-(3-nitrophenyl)-3-butyn-2-ol (MNPB) corresponding to a 75.5% yield and 89.2% selectivity. The crude produce also contained 27.4 grams of 2,7-dimethyl-3,5-octadiyn-2,7-diol and 51.4 grams of a tarry residue containing azo and azoxy compounds.

$$\text{Conversion} = \frac{\text{Initial mole } BNB - \text{Final moles } BNB}{\text{Initial moles } BNB} \times 100$$

$$\text{Selectivity} = \frac{\text{moles } MNPB}{\text{moles } BNB \text{ converted}} \times 100$$

Yield = Conversion × Selectivity

EXAMPLE 2

Example 1 was repeated except 3.7 grams of triphenylphosphine were added to the charge stock. After three hours, the run was essentially complete, the conversion of the nitrobromobenzene being 99.5 weight percent. Gas-liquid chromatographic analysis product using an internal standard procedure showed that the product contained 590.2 grams of 2-methyl-4-(3-nitrophenyl)-3-butyn-2-ol (MNPB) for a yield of 96.0 percent corresponding to a selectivity of 96.4 percent. The remaining product consisted of 2.8 grams of 2,7-dimethyl-3,5-octadiyn-2,7-diol and 0.6 grams of tarry residue. In this Example 2, the molar ratio of the triphenyl phosphine to the palladium was 22:1.

A comparison of Examples 1 and 2 shows that the addition of excess triphenylphosphine to the reaction in accordance with the invention results in a substantial increase in yield from 75.5 to 96.0 and an increase in selectivity from 89.2 to 96.4.

A further series of runs was made which were the same as the run for Example 1 above, except the quantities of materials used were only 1/30th of the quantities of materials used in Examples 1 and 2. The purpose of this series of runs was to vary the molar ratio of the triphenylphosphine to palladium in the reaction mixture and observe the effect of this change. The runs are summarized in Table 1 below.

TABLE 1

| Ex. No. | Pd Salt | (gms) | ⟨C₆H₅⟩₃P (gms) | P/Pd Mole Ratio | Time to 100% Conversion (hrs) | Selectivity | Yield |
|---|---|---|---|---|---|---|---|
| 3 | ((C₆H₅)₃P)₂PdCl₂ | 0.50 | 0 | 2 | 3* | 85 | 85 |
| 4 | " | 0.50 | 0.25 | 8.7 | 1 | 98 | 98 |
| 5 | " | 0.50 | 0.50 | 15.4 | 2.5 | 95 | 91 |
| 6 | " | 0.50 | 1.0 | 28.7 | 6.0 | 90 | 90 |
| 7 | " | 0.50 | 2.0 | 55.5 | 12 | 91 | 91 |
| 8 | PdCl₂ | 0.013 | 0 | 0 | NO REACTION | | |
| 9 | " | 0.013 | 0.50 | 13.4 | 2.5 | 96 | 96 |

*Frequently does not reach 100% conversion

Referring to Table 1 above, Example 3 was the base run, which illustrates the use of the palladium catalyst in accordance with the teachings of Ser. No. 840,553. The conversion of the nitrobromobenzene was substantially complete in three hours, but it is noted that frequently the conversion on a small scale did not reach completion. This was the best run that was observed on a small or large scale showing complete conversion of the charge stock in three hours using the pre-formed palladium catalyst. The selectivity due to formation of the desired NMPB was 85%, and the yield of product was 85%. In Example 4, the molar ratio of triphenylphosphine to palladium was 8.7 which resulted in an overall reaction time of one hour and a selectivity and yield of 98 percent. An increase in the phosphorus to palladium molar ratio to 15.4 (Ex. 5) resulted in an increased reaction time (2.5 hours) and a slight decrease in selectivity to 95 percent, and a corresponding decrease in yield of 95 percent.

Further increases in the molar ratio of phosphorus to palladium (28.7 - Ex. 6; and 55.5 - Ex. 7) resulted in further increases in overall reaction times, with a decrease in selectivity to about the 90% level. It is noted that the results of Example 2 (the larger scale run) show reaction times, selectivities and yields which are about the same as those for Example 5 above.

EXAMPLE 8

Example 3 was repeated except in place of the triphenylphosphine substituted palladium chloride catalyst, 0.13 gram of palladium chloride (PdCl$_2$) was used as the sole catalytic material. No reaction was observed after 22 hours.

EXAMPLE 9

Example 8 was repeated except in addition, 0.50 gram of triphenylphosphine was added initially to the reaction mixture. The triphenylphosphine to palladium mole ratio in the reaction mixture was 13.4. Substantially complete conversion of the nitrobromobenzene was observed after 2½ hours, and the selectivity to the formation of MNPB was 96%, for a corresponding yield of 96%.

A comparison of Example 9 with the runs in Table 1 above shows that the triphenylphosphine palladium complex catalyst can be formed in situ and results in excellent reaction times, selectivities and yield of the desired product.

Resort may be had to such variations and modifications as fall within the spirit of the invention and the scope of the appended claims.

We claim:

1. In a process for the production of a nitrophenyl hydroxy substituted acetylene by reacting a nitrobromobenzene with a substituted terminal acetylene compound containing at least three carbon atoms and an hydroxy group on the carbon atom adjacent to the acetylene group in the presence of a reaction mixture comprising:

(i) a solvent comprising a compound having the formula:

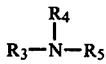

where R$_3$, R$_4$, and R$_5$ can be the same or different and are selected from the group consisting of hydrogen and lower alkyl groups having from 1 to 4 carbon atoms with the proviso that no more than one of said R groups can be hydrogen;

(ii) a catalyst comprising a compound having the formula:

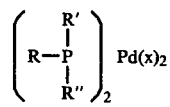

where x can be Br, I, or Cl;
   and where R, R' and R" can be the same or different and are selected from the group consisting of phenyl, substituted phenyl and alkyl groups having from 1 to 4 carbon atoms, and (iii) a promoter comprising cuprous iodide;
   the improvement which comprises reacting said nitrobromobenzene in the added presence of a sufficient amount of excess trisubstituted phosphine over that amount needed to form said catalyst to result in a yield of desired nitrophenyl hydroxy acetylene of at least 90 weight percent.

2. A process in accordance with claim 1 wherein the terminal acetylene compound has the formula:

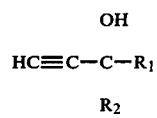

where R$_1$ and R$_2$ can be the same or different and are selected from the group consisting of hydrogen and lower alkyl groups having from 1 to 4 carbon atoms, phenyl and substituted phenyl, and where R$_1$ and R$_2$ can form a saturated 5- or 6-membered ring.

3. A process in accordance with claim 2 wherein R$_1$ and R$_2$ in the terminal acetylene compound are both methyl and wherein the resultant nitrophenyl acetylene is 2-methyl-4(nitrophenyl)3-butyn-2-ol.

4. A process in accordance with claim 3 wherein the nitrobromobenzene is meta-nitrobromobenzene and the resultant nitrophenyl hydroxy acetylene is 2-methyl-4(3-nitrophenyl)3-butyn-2-ol.

5. A process in accordance with claim 1 wherein the mole ratio of said trisubstituted phosphine to palladium in said reaction mixture is from 2.5:1 to 75:1.

6. A process in accordance with claim 5 wherein the mole ratio of said trisubstituted phosphine to palladium in said reaction mixture is from 5:1 to 20:1.

7. A process in accordance with claim 6 wherein the terminal acetylene compound has the formula:

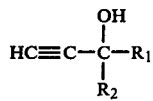

where R$_1$ and R$_2$ can be the same or different and are selected from the group consisting of hydrogen and lower alkyl groups having from 1 to 4 carbon atoms, phenyl and substituted phenyl, and where R$_1$ and R$_2$ can form a saturated 5- or 6-membered ring.

8. A process in accordance with claim 7 wherein R$_1$ and R$_2$ in the terminal acetylene compound are both methyl and wherein the resultant nitrophenyl hydroxy acetylene is 2-methyl-4-(nitrophenyl)-3-butyn-2-ol.

9. A process in accordance with claim 8 wherein the nitrobromobenzene is meta-nitrobromobenzene and the resultant nitrophenyl hydroxy acetylene is 2-methyl-4(3-nitrophenyl)3-butyn-2-ol.

10. A process in accordance with claim 9 wherein the catalyst is bis(triphenylphosphine)palladium dichloride.

11. A process in accordance with claim 6 wherein the solvent is triethylamine.

12. A process in accordance with claim 1 wherein the yield of the desired nitrophenyl hydroxy substituted acetylene is over 95 mole percent.

13. A process in accordance with claim 1 wherein the conversion of said nitrobromobenzene is over 95 weight percent and the selectivity to the formation of the desired nitrophenyl hydroxy substituted acetylene is over 95 weight percent.

14. A process in accordance with claim 13 wherein the nitrobromobenzene is meta-nitrobromobenzene; the catalyst is bis(triphenylphosphine)palladium dichloride; and the solvent is triethylamine.

15. A process in accordance with claim 1 wherein said palladium catalyst is formed in-situ by the reaction of a palladium salt having the formula Pd(X)$_2$ where X is as defined with a trisubstituted phosphine having the formula:

where R, R' and R'' are as defined.

16. A process in accordance with claim 15 wherein the molar ratio of said trisubstituted phosphine to palladium in said reaction mixture is from 5:1 to 20:1.

17. A process in accordance with claim 16 wherein said trisubstituted phosphine is triphenylphosphine.

18. A process in accordance with claim 1 wherein said palladium catalyst is separately formed and added to said reaction mixture and said excess trisubstituted phosphine has the same formula as the trisubstituted phosphine ligands on said palladium catalyst.

19. A process in accordance with claim 18 wherein said trisubstituted phosphine is triphenylphosphine.

20. A process for the production of a substantially pure nitrophenyl hydroxy substituted acetylene which comprises:

(A) reacting a nitrobromobenzene with a substituted terminal acetylene compound containing at least three carbon atoms and an hydroxy group on the carbon atom adjacent to the acetylene group to produce a reaction produce in the presence of a reaction mixture comprising:

(i) a solvent comprising a compound having the formula:

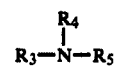

where R$_3$, R$_4$, and R$_5$ can be the same or different and are selected from the group consisting of hydrogen and lower alkyl groups having from 1 to 4 carbon atoms with the proviso that no more than one of said R groups can be hydrogen;

(ii) a catalyst comprising a compound having the formula:

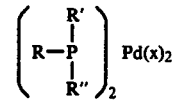

where x can be Br, I, or Cl;
and where R, R' and R'' can be the same or different and are selected from the group consisting of phenyl, substituted phenyl and alkyl groups having from 1 to 4 carbon atoms, and (iii) a promoter comprising cuprous iodide; and
(iv) a trisubstituted phosphine having the formula:

where R, R' and R'' are as defined and wherein the mole ratio of said trisubstituted phosphine to palladium in said reaction mixture is from 5:1 to 20:1;

(B) and thereafter fractionally crystallizing the desired nitrophenyl hydroxy substituted acetylene from said reaction product in substantially pure form.

21. A process in accordance with claim 20 wherein said fractional crystallization occurs in the presence of a solvent consisting of cyclohexane.

* * * * *